(12) United States Patent
Toh et al.

(10) Patent No.: US 7,983,387 B1
(45) Date of Patent: Jul. 19, 2011

(54) METHOD AND SYSTEM TO PREDICT DETECTABILITY AND IDENTIFY FOREIGN OBJECTS

(75) Inventors: Chin Hoi Toh, Orange, CA (US);
Rodney Stephen Wright, Huntington Beach, CA (US); James E. Engel, Newport Beach, CA (US)

(73) Assignee: The Boeing Company, Chicago, IL (US)

( * ) Notice: Subject to any disclaimer, the term of this patent is extended or adjusted under 35 U.S.C. 154(b) by 144 days.

(21) Appl. No.: 12/582,359

(22) Filed: Oct. 20, 2009

(51) Int. Cl.
*G01N 23/04* (2006.01)
*G01N 23/201* (2006.01)
*G01B 15/02* (2006.01)
(52) U.S. Cl. .............. 378/57; 378/86; 378/89
(58) Field of Classification Search .......... 378/57, 378/86, 87, 88, 89, 6, 7, 50, 54, 70
See application file for complete search history.

(56) References Cited

U.S. PATENT DOCUMENTS 6,122,344 A * 9/2000 Beevor ............................ 378/88
2008/0253637 A1 * 10/2008 Boyden et al. ................. 382/131

OTHER PUBLICATIONS

"I.C. Contrast and Image Formation", pp. 1-7, retrieved Sep. 10, 2009 http://em-outreach.ucsd.edu/web-course/Sec-I.C/Sec-I.C.html.
"Z Backscatter: power, effectiveness and safety", pp. 1-4, retrieved Sep. 10, 2009 http://www.as-e.com/products_solutions/Z_backscatter.asp.

* cited by examiner

*Primary Examiner* — Irakli Kiknadze
(74) *Attorney, Agent, or Firm* — Yee & Associates, P.C.

(57) ABSTRACT

The different advantageous embodiments provide a system for identifying a likelihood of detecting objects with a backscatter x-ray system comprising a structure having a number of objects, a plurality of databases, and a processor unit configured to execute a detection analysis process. The processor unit executes the detection analysis process to identify the number of objects, identify a number of densities associated with each of the number of objects, determine a likelihood of detecting each of the number of objects with the backscatter x-ray system, and generate a three-dimensional diagram of the likelihood of detecting each of the number of objects.

25 Claims, 10 Drawing Sheets

CHEMICAL ELEMENTS AND
RELATED DENSITITES
600

CHEMICAL ELEMENTS
602

REFERENCE
DENSITIES, g/cm3
604

| Atomic Numbers 606 | Chemical Elements | Reference Densities |
|---|---|---|
| 100 | URANIUM, PLUTONIUM | URANIUM = 19.0 |
| 90 | MERCURY, LEAD | MERCURY = 13.5; LEAD = 11.4 |
| 80 | TUNGSTEN, PLATINUM, GOLD | TUNGSTEN = 19.3; PLATINUM = 21.5; GOLD = 19.3 |
| 70 | | |
| 60 | TIN | TIN = 7.3 |
| 50 | MOLYBDENUM, NIOBIUM, ZIRCONIUM, SILVER | SILVER = 10.5 |
| 40 | GALLIUM, GERMANIUM, ARSENIDE, YTTRIUM | GALLIUM = 5.9; GERMANIUM = 5.3 |
| 30 | TITANIUM, IRON, COPPER, NICKEL, CHROMIUM, COBALT, MANGANESE, VANADIUM, ZINC | TITANIUM = 4.5; IRON = 7.9; COPPER = 8.9; ZINC = 7.1 |
| 20 | ALUMINUM, MAGNESIUM, SILICONE, SODIUM, CHLORINE | ALUMINIUM = 2.7; SILICONE = 2.3; SODIUM = 0.97; CHLORINE = 0.003 |
| 10 | HYDROGEN, CARBON, NITROGEN, OXYGEN | AIR = 0.0012; TYPICAL WOOD = 0.65; WATER = 1.0; PLASTICS = 0.9-1.4; CARBON COMPOSITES = 1.5-1.9 |
| 0 | | |

*FIG. 6*

OBJECTS RELATED TO
CHEMICAL ELEMENTS
700

| | CHEMICAL ELEMENTS 702 | CORRESPONDING OBJECTS 704 |
|---|---|---|
| 100 | URANIUM, PLUTONIUM | |
| 90 | MERCURY, LEAD | |
| 80 | TUNGSTEN, PLATINUM, GOLD | ELECTRONICS |
| 70 | | |
| 60 | TIN | ELECTRONICS |
| 50 | MOLYBDENUM, NIOBIUM, ZIRCONIUM, SILVER | ELECTRONICS |
| 40 | GALLIUM, GERMANIUM, ARSENIDE, YTTRIUM | AVIONICS/ELECTRONICS |
| 30 | TITANIUM, IRON, COPPER, NICKEL, CHROMIUM, COBALT, MANGANESE, VANADIUM, ZINC | FASTENERS, HAND TOOLS, DRILL BITS, BOLTS/NUTS |
| 20 | ALUMINUM, MAGNESIUM, SILICONE, SODIUM, CHLORIDE | DIRT, SALT WATER, ALUMINIUM-ALLOY, RIVETS, SKINS, FRAMES |
| 10 | HYDROGEN, CARBON, NITROGEN, OXYGEN | PLASTIC, PAPER, WOOD, FOOD, TREE LEAVES, FRESH WATER, CLOTH, OIL, BioFOD (INSECTS), OTHER ORGANIC MATERIAL |
| 0 | | |

ATOMIC NUMBERS 706

*FIG. 7*

METHOD AND SYSTEM TO PREDICT DETECTABILITY AND IDENTIFY FOREIGN OBJECTS

BACKGROUND INFORMATION

1. Field

The present disclosure relates generally to nondestructive inspection and in particular to using backscatter x-rays in nondestructive inspection. Still more particularly, the present disclosure relates to detection of objects using backscatter x-rays.

2. Background

Unidentified objects in an aircraft structure are undesirable during operation of the aircraft. Objects may be located within areas of an aircraft that are hard to reach or inaccessible, such as enclosed in a sealed area or within a structural component of the aircraft, for example. Detecting and identifying objects in these hard to reach or inaccessible areas of the aircraft may be difficult and even impossible without disassembly of the aircraft structure.

Nondestructive inspection is a range of analysis techniques used to evaluate properties of an object without causing changes or inconsistencies in the object. The object may be a part, component, system, or some other suitable object. One common technique used for nondestructive inspection is radiographic imaging. Radiographic imaging uses x-ray machines, or some other radioactive source, as a source of photons. Radiographic imaging detects and measures the reaction of photons to the material, component, or system being tested.

X-ray systems detect transmission of photons through an object to form an image. Photons generally interact with objects by either passing through an object, being absorbed by the object, or being scattered from the object. The greater the density of an object, the more photons are either blocked or absorbed rather than passing through. In contrast, when an object is less dense more photons are able to pass through the object as compared to objects that are more dense.

Backscatter x-ray systems detect radiation, or photons, that come back from a target, rather than detecting transmission of photons through a target as with traditional x-ray machines. Backscatter x-ray systems form images based on how photons scatter when encountering an object. Because of this difference, backscatter x-ray systems have potential applications in situations where non-destructive examination is required but only one side is available for examination. One situation where backscatter x-ray systems are useful is in searching containers and vehicles. Some backscatter x-ray systems are able to penetrate up to three centimeters of solid steel, providing search access to sealed or hard to reach areas.

Therefore, it would be advantageous to have a method and apparatus that takes into account one or more of the issues discussed above, as well as possibly other issues.

SUMMARY

The different advantageous embodiments provide a system for identifying a likelihood of detecting objects with a backscatter x-ray system comprising a structure having a number of objects, a plurality of databases, and a processor unit configured to execute a detection analysis process. The processor unit executes the detection analysis process to identify the number of objects, identifies a number of densities associated with each of the number of objects, determines a likelihood of detecting each of the number of objects with the backscatter x-ray system, and generates a three-dimensional diagram of the likelihood of detecting each of the number of objects.

The different advantageous embodiments further provide a system for identifying objects after the objects have been detected, comprising a structure having an unidentified object, a detector, a plurality of databases, and a processor unit configured to execute a detection analysis process. The detector is configured to detect the unidentified object and generate an image of the unidentified object. The processor unit executes the detection analysis process to identify a photon reaction result associated with the detection of the unidentified object using the image, identify a density of the unidentified object based on a comparison of the photon reaction result identified in the image with other photon reaction results identified in stored images, identify a number of chemical elements associated with the density, identify an atomic number associated with the number of chemical elements identified and the photon reaction result identified, and generate an identification of a number of foreign objects that correspond with the number of chemical elements, the atomic number, and the density of the unidentified object.

The different advantageous embodiments further provide a method for identifying a likelihood of detecting objects with a backscatter x-ray system. A number of objects are identified using a processor unit. A number of densities associated with each of the number of objects are identified using a number of chemical elements associated with each of the number of objects. A likelihood of detecting each of the number of objects with the backscatter x-ray system is determined using the number of densities and an atomic number associated with each of the number of objects. A three-dimensional diagram of the likelihood of detecting each of the number of objects with the backscatter x-ray system is generated.

The different advantageous embodiments further provide a method for identifying objects after the objects have been detected. An unidentified object is detected using a backscatter x-ray system to form an image. The photon reaction result associated with the detection of the unidentified object is identified using the image. The density of the unidentified object is identified based on a comparison of the photon reaction result identified in the image with other photon reaction results identified in stored images. An identification of a number of foreign objects associated with the density and the photon reaction result identified is generated.

achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

FIG. 6 is an illustration of chemical elements and related densities in accordance with an advantageous embodiment;

FIG. 7 is an illustration of objects related to chemical elements in accordance with an advantageous embodiment;

DETAILED DESCRIPTION

Figure 1:
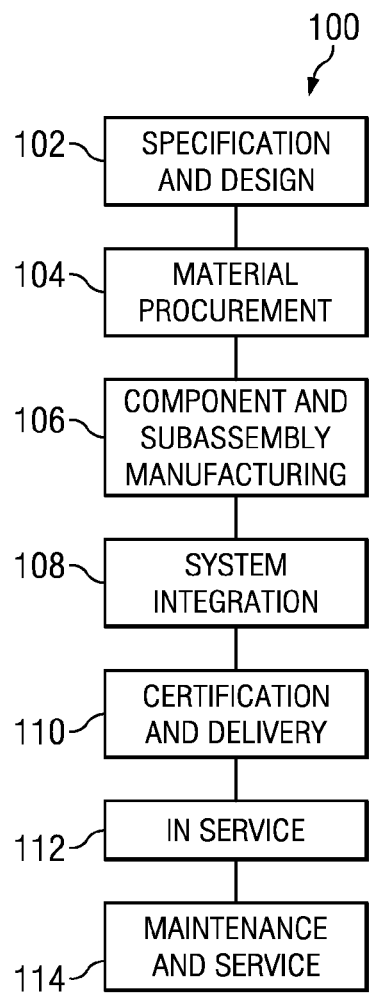
FIG. 1 is an illustration of an aircraft manufacturing and service method in accordance with an advantageous embodiment.
Figure 2:
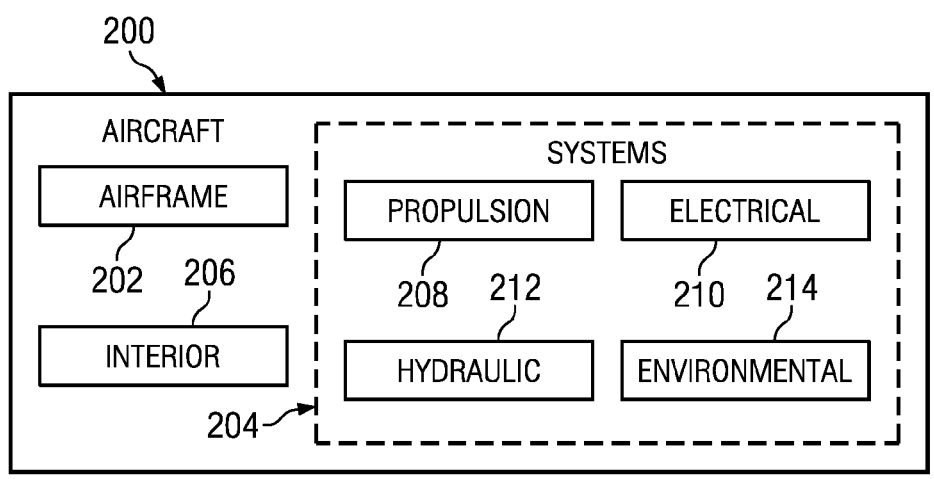
FIG. 2 is illustration of an aircraft in which an advantageous embodiment may be implemented.

Referring more particularly to the drawings, embodiments of the disclosure may be described in the context of the aircraft manufacturing and service method 100 as shown in FIG. 1 and aircraft 200 as shown in FIG. 2. Turning first to FIG. 1, an illustration of an aircraft manufacturing and service method is depicted in accordance with an advantageous embodiment. During pre-production, aircraft manufacturing and service method 100 may include specification and design 102 of aircraft 200 in FIG. 2 and material procurement 104.

During production, component and subassembly manufacturing 106 and system integration 108 of aircraft 200 in FIG. 2 may take place. Thereafter, aircraft 200 in FIG. 2 may go through certification and delivery 110 in order to be placed in service 112. While in service by a customer, aircraft 200 in FIG. 2 may be scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of venders, subcontractors, and suppliers; and an operator may be an airline, leasing company, military entity, service organization, and so on.

With reference now to FIG. 2, an illustration of an aircraft is depicted in which an advantageous embodiment may be implemented. In this example, aircraft 200 may be produced by aircraft manufacturing and service method 100 in FIG. 1 and may include airframe 202 with a plurality of systems 204 and interior 206. Examples of systems 204 may include one or more of propulsion system 208, electrical system 210, hydraulic system 212, and environmental system 214. Any number of other systems may be included. Although an aerospace example is shown, different advantageous embodiments may be applied to other industries, such as the automotive industry. Additionally, different advantageous embodiments may be applied to other infrastructure industries, such as bridges and buildings or other civilian or military applications.

Apparatus and methods embodied herein may be employed during any one or more of the stages of aircraft manufacturing and service method 100 in FIG. 1. For example, components or subassemblies produced in component and subassembly manufacturing 106 in FIG. 1 may be inspected while aircraft 200 is in maintenance and service 114 in FIG. 1.

Also, one or more apparatus embodiments, method embodiments, or a combination thereof may be utilized during service stages, such as maintenance and service 114 and in service 112 in FIG. 1, for example, without limitation, by substantially expediting the inspection and/or maintenance of aircraft 200. For example, the different advantageous embodiments may expedite the inspection of aircraft 200 by providing detection of a number of objects within an enclosed area of aircraft 200. This detection may be performed within a desired amount of time and without requiring disassembly of aircraft 200 to physically expose the enclosed area. In another illustrative example, the different advantageous embodiments may expedite the inspection and/or maintenance of aircraft 200 by providing an identification of the detectability by a backscatter x-ray system of each of a number of objects used during maintenance that may need to be accounted for prior to the conclusion of maintenance processes.

As used herein, the phrase "at least one of", when used with a list of items, means that different combinations of one or more of the items may be used and only one of each item in the list may be needed. For example, "at least one of item A, item B, and item C" may include, for example, without limitation, item A or item A and item B. This example also may include item A, item B, and item C, or item B and item C.

The different advantageous embodiments recognize and take into account a number of different considerations. For example, the different advantageous embodiments take into account and recognize that currently used systems do not provide a three-dimensional visual diagram to identify the detectability of objects in enclosed spaces or areas, such as within an aircraft structure.

Thus, the different advantageous embodiments provide a system for identifying a likelihood of detecting objects with a backscatter x-ray system comprising a structure having a number of objects, a plurality of databases, and a processor unit configured to execute a detection analysis process. The processor unit executes the detection analysis process to identify the number of objects, identify a number of densities associated with each of the number of objects, determine a likelihood of detecting each of the number of objects with the backscatter x-ray system, and generate a three-dimensional diagram of the likelihood of detecting each of the number of objects.

The different advantageous embodiments further provide a system for identifying objects after the objects have been detected, comprising a structure having an unidentified object, a detector, a plurality of databases, and a processor unit configured to execute a detection analysis process. The detector is configured to detect the unidentified object and generate an image of the unidentified object. The processor unit executes the detection analysis process to identify a photon reaction result associated with the detection of the unidentified object using the image, identify a density of the unidentified object based on a comparison of the photon reaction result identified in the image with other photon reaction results identified in stored images, identify a number of chemical elements associated with the density, identify an atomic number associated with the number of chemical elements identified and the photon reaction result identified, and generate an identification of a number of foreign objects that correspond with the number of chemical elements, the atomic number, and the density of the unidentified object.

The different advantageous embodiments further provide a method for identifying a likelihood of detecting objects with a backscatter x-ray system. A number of objects are identified using a processor unit. A number of densities associated with each of the number of objects are identified using a number of chemical elements associated with each of the number of objects. A likelihood of detecting each of the number of objects with the backscatter x-ray system is determined using the number of densities and an atomic number associated with the each of the number of objects. A three-dimensional diagram of the likelihood of detecting the number of objects with the backscatter x-ray system is generated.

The different advantageous embodiments further provide a method for identifying objects after the objects have been detected. An unidentified object is detected using a backscatter x-ray system to form an image. The photon reaction result associated with the detection of the unidentified object is identified using the image. The density of the unidentified object is identified based on a comparison of the photon reaction result identified in the image with other photon reaction results identified in stored images. An identification of a number of foreign objects associated with the density and the photon reaction result identified is generated.

Figure 3:
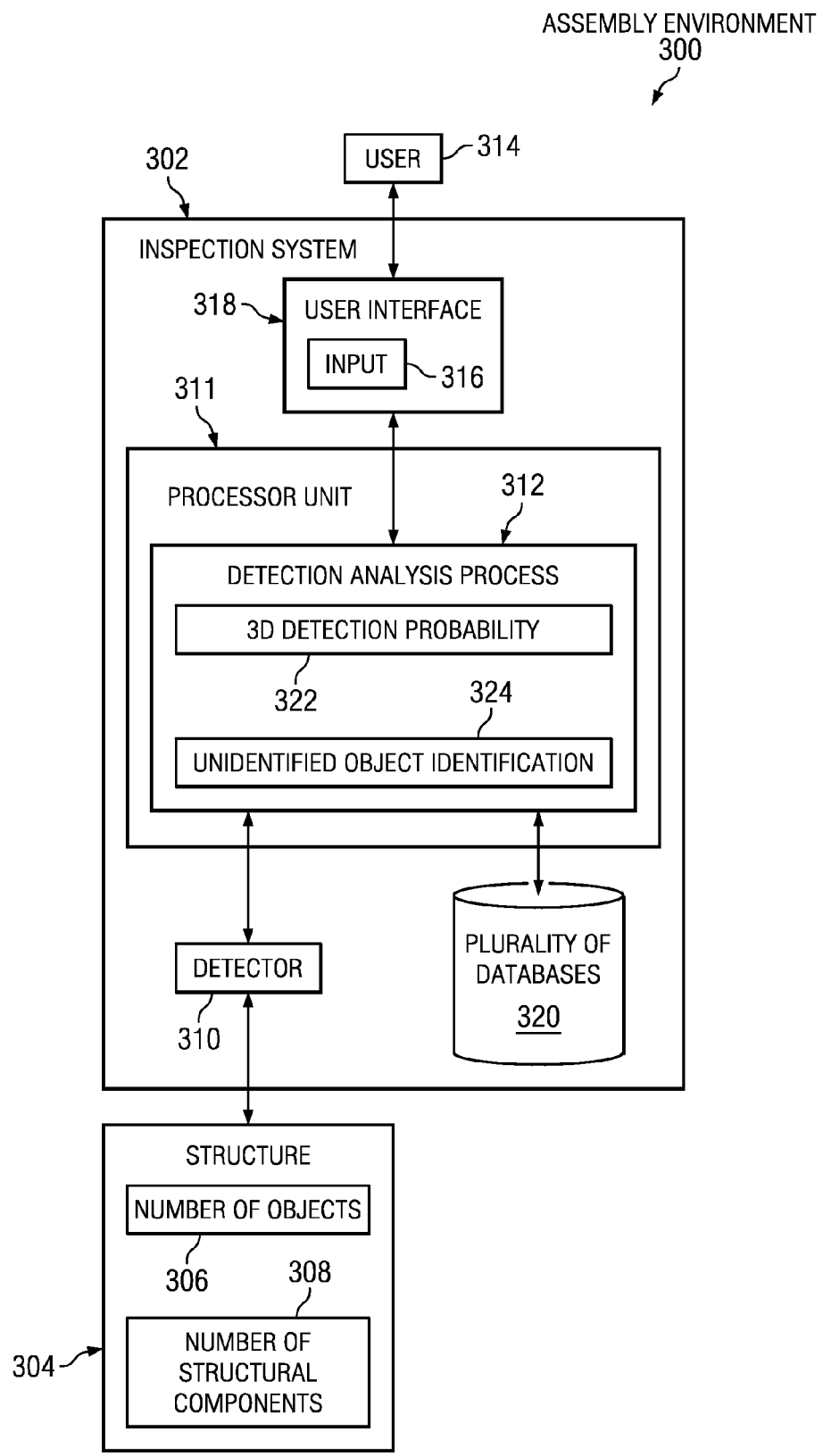
FIG. 3 is an illustration of an assembly environment in accordance with an advantageous embodiment.

With reference now to FIG. 3, an illustration of an assembly environment is depicted in accordance with an advantageous embodiment. Assembly environment 300 may be implemented during one or more of specification and design 102, material procurement 104, component and subassembly manufacturing 106, system integration 108, certification and delivery 110, and/or maintenance and service 114 of aircraft 200 in FIG. 2, for example.

Assembly environment 300 includes inspection system 302 and structure 304. Inspection system 302 may be used to inspect structure 304 for number of objects 306. Number of objects 306 are objects that are not expected or intended to be in structure 304. Number of objects 306 may include, for example, without limitation, electronics, avionics, fasteners, hand tools, drill bits, bolts, nuts, dirt, salt water, fresh water, aluminum-alloy components, rivets, skins, frames, plastic, paper, wood, food, tree leaves, cloth, oil, insects, other organic material, and/or any other object not intended as part of structure 304. Structure 304 may include number of structural components 308. Number of structural components 308 may include, for example, without limitation, composites, alloys, metals, electronics, fasteners, bolts, nuts, rivets, skins, frames, and/or any other suitable component intended as part of structure 304.

Inspection system 302 includes detector 310 and processor unit 311. Processor unit 311 is configured to execute detection analysis process 312. Detector 310 may be, for example, without limitation, a backscatter x-ray detector. Detection analysis process 312 may receive input from detector 310 and/or user 314, such as input 316 received from user 314 via user interface 318. User 314 interacts with inspection system 302 via user interface 318. In an illustrative example, input 316 may describe number of objects 306. Detection analysis process 312 receives input 316 from user 314 in this example and uses input 316 together with plurality of databases 320 to form three-dimensional detection probability 322. Three-dimensional detection probability 322 is a three-dimensional visual diagram of the likelihood that each of number of objects 306 can be detected within structure 304 using detector 310, in this example. For example, three-dimensional detection probability 322 may indicate that a sealant bottle is more likely to be detected than a latex glove. Three-dimensional detection probability 322 may be displayed to user 314 via user interface 318.

In another illustrative example, detection analysis process 312 may receive input from detector 310 detecting number of objects 306 in structure 304. In this example, detection analysis process 312 uses the input 316 and plurality of databases 320 to form unidentified object identification 324. Unidentified object identification 324 includes a number of object identifications that correspond to the information received for number of objects 306 detected by detector 310. For example, unidentified object identification 324 may include a list of three different objects, such as drill bits, bolts, and nuts, for example, as objects that correspond to the detected reaction of photons to the unidentified object combined with the atomic number and/or chemical elements associated with the detected reaction of photons.

Plurality of databases 320 may include information on, for example, without limitation, a number of chemical elements, atomic numbers, mass densities, object materials, and/or any other suitable information for use in forecasting detection of foreign objects and identifying detected foreign objects.

The illustration of assembly environment 300 in FIG. 3 is not meant to imply physical or architectural limitations to the manner in which different advantageous embodiments may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

Figure 4:
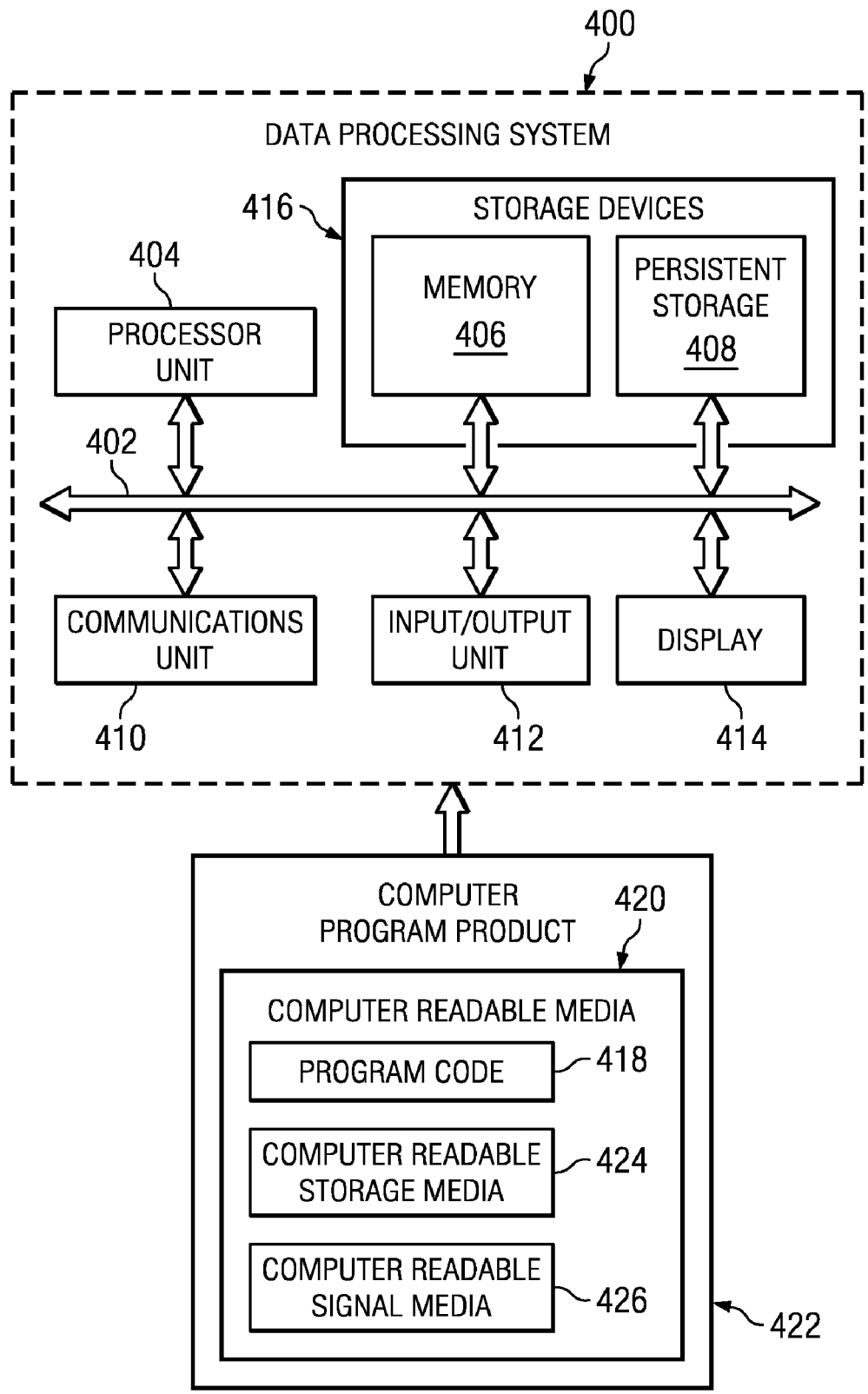
FIG. 4 is an illustration of a data processing system in accordance with an advantageous embodiment.

With reference now to FIG. 4, an illustration of a data processing system is depicted in accordance with an advantageous embodiment. Data processing system 400 may be used to implement different computers and data processing systems within inspection system 302 in FIG. 3.

In this illustrative example, data processing system 400 includes communications fabric 402, which provides communications between processor unit 404, memory 406, persistent storage 408, communications unit 410, input/output (I/O) unit 412, and display 414. Depending on the particular implementation, different architectures and/or configurations of data processing system 400 may be used.

Processor unit 404 serves to execute instructions for software that may be loaded into memory 406. Processor unit 404 may be a set of one or more processors or may be a multi-processor core, depending on the particular implementation. Further, processor unit 404 may be implemented using one or more heterogeneous processor systems in which a main processor is present with secondary processors on a single chip. As another illustrative example, processor unit 404 may be a symmetric multi-processor system containing multiple processors of the same type.

Memory 406 and persistent storage 408 are examples of storage devices 416. A storage device may be any piece of hardware that may be capable of storing information, such as, for example without limitation, data, program code in functional form, and/or other suitable information either on a temporary basis and/or a permanent basis. Memory 406, in these examples, may be, for example, a random access memory or any other suitable volatile or non-volatile storage device. Persistent storage 408 may take various forms depending on the particular implementation. For example, persistent storage 408 may contain one or more components or devices. For example, persistent storage 408 may be a hard drive, a flash memory, a rewritable optical disk, a rewritable magnetic tape, or some combination of the above. The media used by persistent storage 408 also may be removable. For example, a removable hard drive may be used for persistent storage 408.

Communications unit 410, in these examples, provides for communications with other data processing systems or devices. In these examples, communications unit 410 may be a network interface card. Communications unit 410 may provide communications through the use of either or both physical and wireless communications links.

Input/output unit 412 allows for input and output of data with other devices that may be connected to data processing system 400. For example, input/output unit 412 may provide a connection for user input through a keyboard, a mouse, and/or some other suitable input device. Further, input/output unit 412 may send output to a printer. Display 414 provides a mechanism to display information to a user.

Instructions for the operating system, applications and/or programs may be located in storage devices 416, which are in communication with processor unit 404 through communications fabric 402. In these illustrative examples the instructions are in a functional form on persistent storage 408. These instructions may be loaded into memory 406 for execution by processor unit 404. The processes of the different embodiments may be performed by processor unit 404 using computer implemented instructions, which may be located in a memory, such as memory 406.

These instructions are referred to as program code, computer usable program code, or computer readable program code that may be read and executed by a processor in processor unit 404. The program code in the different embodiments may be embodied on different physical or tangible computer readable media, such as memory 406 or persistent storage 408.

Program code 418 may be located in a functional form on computer readable media 420 that may be selectively removable and may be loaded onto or transferred to data processing system 400 for execution by processor unit 404. Program code 418 and computer readable media 420 form computer program product 422 in these examples. In one example, computer readable media 420 may be in a tangible form, such as, for example, an optical or magnetic disc that may be inserted or placed into a drive or other device that may be part of persistent storage 408 for transfer onto a storage device, such as a hard drive that may be part of persistent storage 408. In a tangible form, computer readable media 420 also may take the form of a persistent storage, such as a hard drive, a thumb drive, or a flash memory that may be connected to data processing system 400. The tangible form of computer readable media 420 may also be referred to as computer recordable storage media. In some instances, computer readable media 420 may not be removable.

Alternatively, program code 418 may be transferred to data processing system 400 from computer readable media 420 through a communications link to communications unit 410 and/or through a connection to input/output unit 412. The communications link and/or the connection may be physical or wireless in the illustrative examples. The computer readable media also may take the form of non-tangible media, such as communications links or wireless transmissions containing the program code.

In some illustrative embodiments, program code 418 may be downloaded over a network to persistent storage 408 from another device or data processing system for use within data processing system 400. For instance, program code stored in a computer readable storage medium in a server data processing system may be downloaded over a network from the server to data processing system 400. The data processing system providing program code 418 may be a server computer, a client computer, or some other device capable of storing and transmitting program code 418.

The different components illustrated for data processing system 400 are not meant to provide architectural limitations to the manner in which different embodiments may be implemented. The different illustrative embodiments may be implemented in a data processing system including components in addition to or in place of those illustrated for data processing system 400. Other components shown in FIG. 4 can be varied from the illustrative examples shown. The different embodiments may be implemented using any hardware device or system capable of executing program code. As one example, the data processing system may include organic components integrated with inorganic components and/or may be comprised entirely of organic components excluding a human being. For example, a storage device may be comprised of an organic semiconductor.

As another example, a storage device in data processing system 400 may be any hardware apparatus that may store data. Memory 406, persistent storage 408 and computer readable media 420 are examples of storage devices in a tangible form.

In another example, a bus system may be used to implement communications fabric 402 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 406 or a cache such as found in an interface and memory controller hub that may be present in communications fabric 402.

Figure 5:
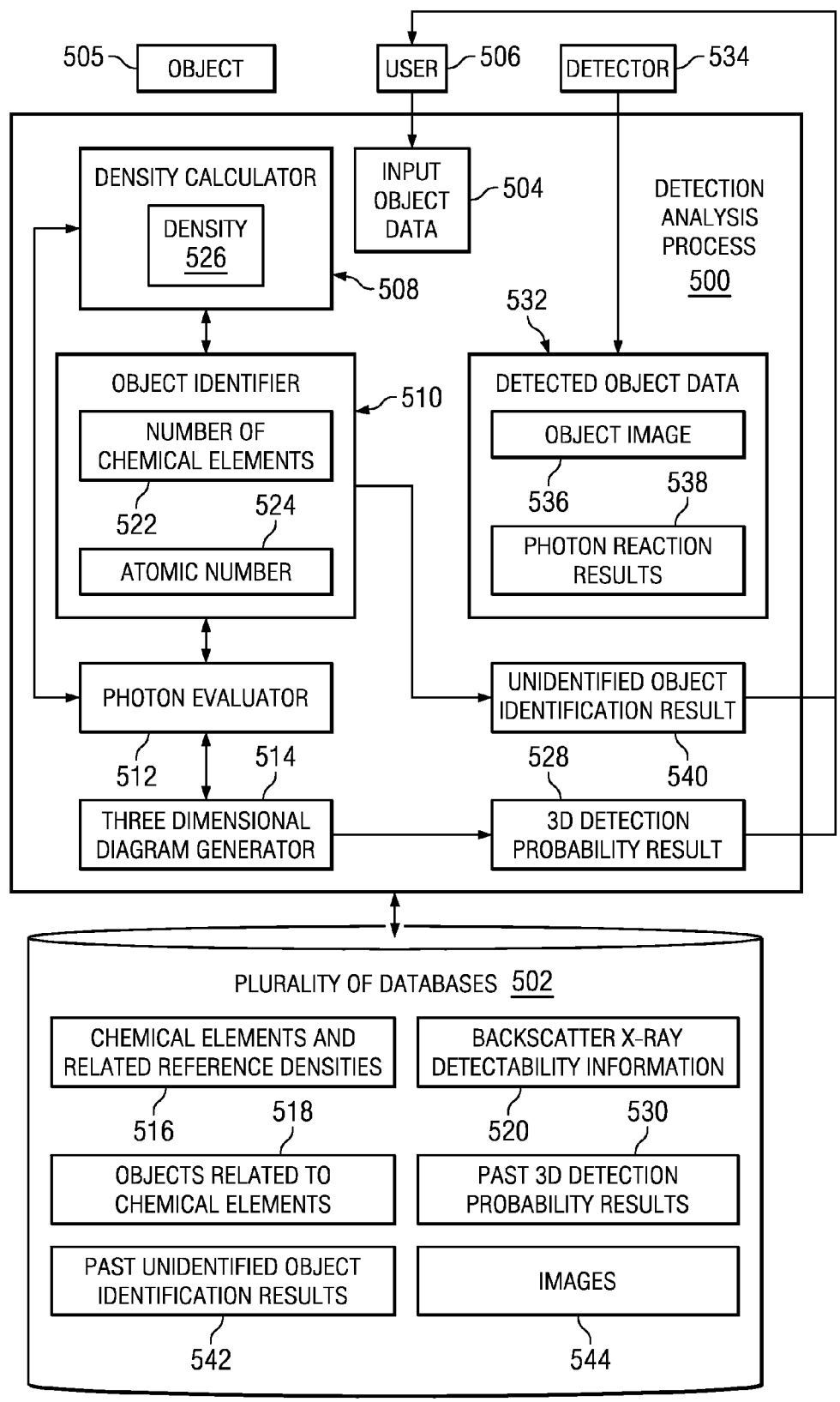
FIG. 5 is an illustration of a detection analysis process in accordance with an advantageous embodiment.

With reference now to FIG. 5, an illustration of a detection analysis process is depicted in accordance with an advantageous embodiment. Detection analysis process 500 is an illustrative example of one implementation of detection analysis process 312 in FIG. 3.

Plurality of databases 502 is an illustrative example of one implementation of plurality of databases 320 in FIG. 3. Detection analysis process 500 receives input object data 504 from user 506. Input object data 504 is an identification of a specific object, such as object 505, input by user 506. Object 505 may be, for example, an unexpected or unintended object for a structure, such as number of objects 306 in FIG. 3. User 506 may require a result indicating the likelihood of detecting object 505 within a structure, such as structure 304 in FIG. 3, for example.

Detection analysis process 500 includes density calculator 508, object identifier 510, photon evaluator 512, and three-dimensional diagram generator 514. Detection analysis process 500 receives input object data 504 and retrieves information from plurality of databases 502. Plurality of databases 502 may include, for example, without limitation, chemical elements and related reference densities 516, objects related to chemical elements 518, backscatter x-ray detectability information 520, images 544 and/or any other suitable information.

Chemical elements and related reference densities 516 includes a number of chemical elements, the atomic numbers for each of the chemical elements, and a measurement of density for each of the number of chemical elements at a standard temperature and pressure. For example, chemical elements and related reference densities 516 may include uranium and identify the exact atomic number of uranium as ninety-two from the referenced chemical element Periodic Table, with an associated density of nineteen grams per cubed centimeter, for example.

Objects related to chemical elements 518 includes an identification of a number of objects, chemical elements associated with each of the number of objects, and the atomic numbers for each of the chemical elements. For example, objects related to chemical elements 518 may identify one object as electronics and associate a number of chemical elements with electronics, including tin, molybdenum, niobium, zirconium, silver, tungsten, platinum, and gold. In this example, the atomic number for the chemical element of tin is fifty, while the atomic numbers for the chemical elements of tungsten, platinum, and gold are seventy-four, seventy-eight, and seventy-nine, respectively from the referenced chemical element Periodic Table.

Backscatter x-ray detectability information 520 includes information about the reaction of photons to a number of different objects and/or associated with a number of atomic numbers. Images 544 includes prior object images generated by detector 534. The prior object images include associated photon counts and density data determined in previous analysis by detection analysis process 500.

Object identifier 510 uses objects related to chemical elements 518 to identify number of chemical elements 522 for object 505. Object identifier 510 may also identify atomic number 524 for number of chemical elements 522. Density calculator 508 uses atomic number 524 and number of chemical elements 522 identified by object identifier 510 along with chemical elements and related reference densities 516 to calculate density 526 of object 505.

Photon evaluator 512 receives number of chemical elements 522, atomic number 524, and density 526 of input object data 504 from object identifier 510 and density calculator 508. Photon evaluator 512 uses backscatter x-ray detectability information 520 to determine the likelihood that object 505 can be detected using a backscatter x-ray system, such as detector 310 in FIG. 3, for example. Three-dimensional diagram generator 514 uses the information identified and calculated by density calculator 508, object identifier 510, and photon evaluator 512 to create three-dimensional detection probability result 528.

Three-dimensional detection probability result 528 is a three-dimensional diagram of the likelihood that object 505 can be detected, such as three-dimensional detection probability 322 in FIG. 3, for example.

Three-dimensional detection probability result 528 may be displayed to user 506 via a user interface, such as user interface 318 in FIG. 3, for example. Detection analysis process 500 may also store three-dimensional detection probability result 528 in past three-dimensional detection probability results 530 in plurality of databases 502. Each of the three-dimensional detectability diagrams stored in past three-dimensional detection probability results 530 include both images and data strings for future references. Past three-dimensional detection probability results 530 may be used by detection analysis process 500 in future operations when object 505 is recognized by detection analysis process 500 as having an associated stored result, for example. In the illustrative example where there is no one-to-one corresponding match, the system may plot the newly detected data point on the existing three-dimensional diagram that closely represents the detected object, and display the modified diagram to the user for determination. In another illustrative example, the system may displays the new data within the nearest matches found in plurality of databases 502 to show the newly detected object as fitting between two previously identified items in a diagram, such as paper and cardboard, for example.

Detection analysis process 500 may receive detected object data 532 from detector 534. Detector 534 is an illustrative example of one implementation of detector 310 in FIG. 3. Detector 534 may detect object 505 in a structure, such as structure 304 in FIG. 3, for example. Detector 534 may send detected object data 532 to detection analysis process 500. Detected object data 532 may include object image 536 and photon reaction results 538. Object image 536 is the image generated by detector 534 when detecting object 505. Photon reaction results 538 is the detected reaction of photons interacting with object 505 in object image 536. The photon reaction to object 505 may include, for example, without limitation, scatter power, pattern of photons, pass through of photons, absorption of photons, bounce-back of photons, and/or any other suitable photon reaction detected by detector 534.

Photon evaluator 512 uses backscatter x-ray detectability information 520 to identify a number of potential objects and/or atomic numbers for object 505 based on photon reaction results 538. Density calculator 508 compares object image 536 with stored images retrieved from images 544 in plurality of databases 502 to determine an associated density for object 505 detected by detector 534. Density calculator 508 uses chemical elements and related reference densities 516 to determine a number of potential chemical elements for object 505 based on the density determined and/or the number of atomic numbers identified by photon evaluator 512. Object identifier 510 uses objects related to chemical elements 518 to form unidentified object identification result 540 based on the number of chemical elements identified by density calculator 508 and the number of potential objects and/or atomic numbers identified by photon evaluator 512. Detection analysis process 500 may also store unidentified object identification result 540 in past unidentified object identification results 542 in plurality of databases 502. Detection analysis process 500 stores object image 536 with the associated density identified by density calculator 508 in images 544. Past unidentified object identification results 542 and images 544 may be used by detection analysis process 500 in future operations when detected object data 532 is recognized by detection analysis process 500 as having an associated stored result, for example.

The illustration of detection analysis process 500 in FIG. 5 is not meant to imply physical or architectural limitations to the manner in which different advantageous embodiments may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

With reference now to FIG. 6, an illustration of chemical elements and related densities is depicted in accordance with an advantageous embodiment. Chemical elements and related densities 600 is an illustrative example of one implementation of chemical elements and related reference densities 516 of plurality of databases 502 in FIG. 5.

Chemical elements and related densities 600 include chemical elements 602, reference densities g/cm3 604, and atomic numbers 606. Atomic numbers 606 depicts a scaled interval of ten for illustrative purposes, and is not meant to limit the different advantageous embodiments whatsoever. The system may use a reference chemical element Periodic Table to identify the exact atomic number for a given chemical element that sits within an atomic number range, such as the range represented in atomic numbers 606, for example. Chemical elements and related densities 600 is used by detection analysis process 500 in FIG. 5 to identify related densities for chemical elements and/or atomic numbers of chemical elements, for example.

The illustration of chemical elements and related densities 600 in FIG. 6 is not meant to imply physical or architectural limitations to the manner in which different advantageous embodiments may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

With reference now to FIG. 7, an illustration of objects related to chemical elements is depicted in accordance with an advantageous embodiment. Objects related to chemical elements 700 is an illustrative example of one implementation of objects related to chemical elements 518 of plurality of databases 502 in FIG. 5.

Objects related to chemical elements 700 includes chemical elements 702, corresponding objects 704, and atomic numbers 706. Atomic numbers 706 depicts a scaled interval of ten for illustrative purposes, and is not meant to limit the different advantageous embodiments whatsoever. The system may use a reference chemical element Periodic Table to identify the exact atomic number for a given chemical element that sits within an atomic number range, such as the range represented in atomic numbers 706, for example. Objects related to chemical elements 700 is used by detection analysis process 500 in FIG. 5 to identify possible objects associated with chemical elements and/or atomic numbers, for example.

The illustration of objects related to chemical elements 700 in FIG. 7 is not meant to imply physical or architectural limitations to the manner in which different advantageous embodiments may be implemented. Other components in addition and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

Figure 8:
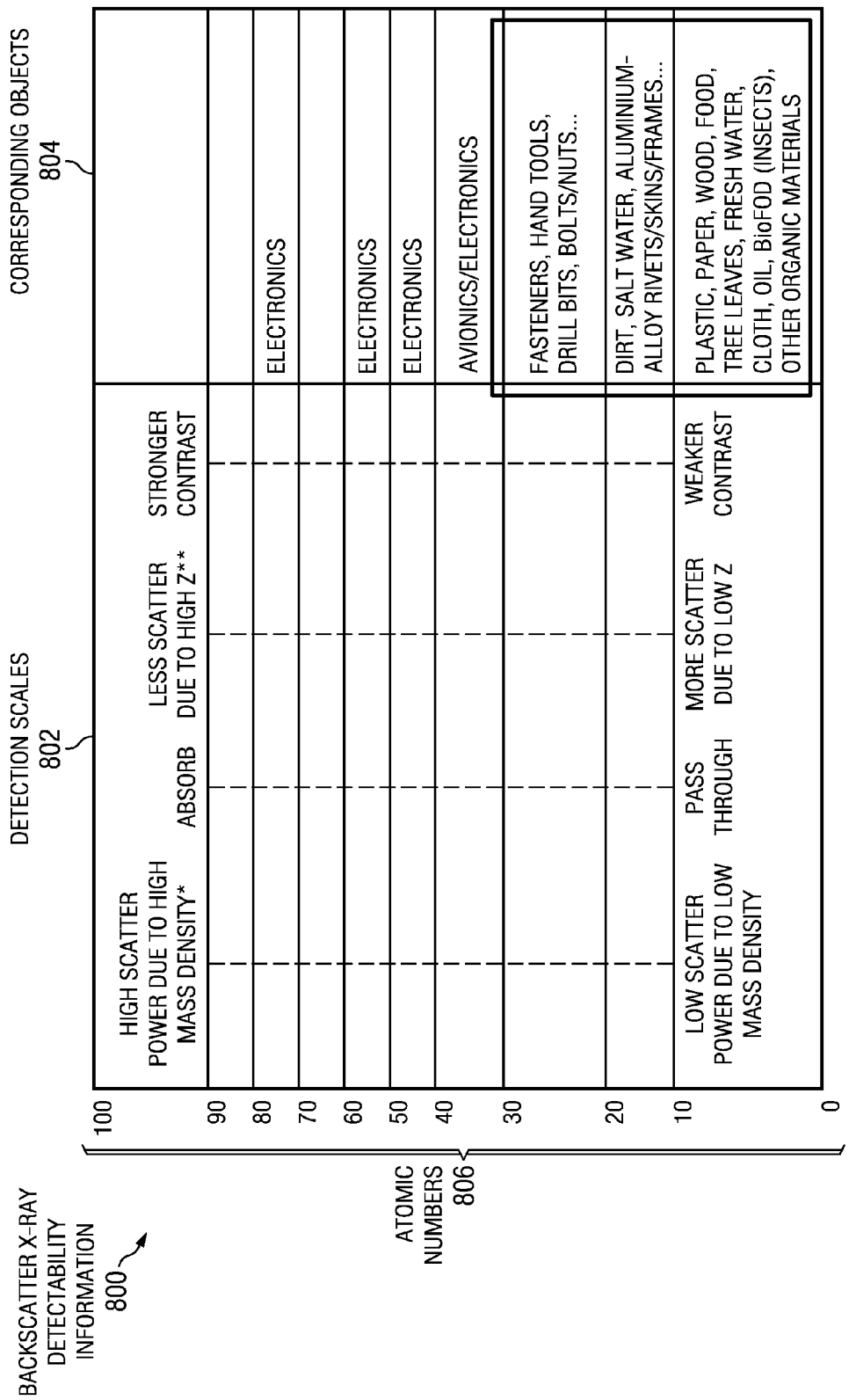
FIG. 8 is an illustration of backscatter x-ray detectability information in accordance with an advantageous embodiment.

With reference now to FIG. 8, an illustration of backscatter x-ray detectability information is depicted in accordance with an advantageous embodiment. Backscatter x-ray detectability information 800 is an illustrative example of one implementation of backscatter x-ray detectability information 520 of plurality of databases 502 in FIG. 5.

Backscatter x-ray detectability information 800 includes detection scales 802, corresponding objects 804, and atomic numbers 806. Backscatter x-ray detectability information 800 is used by detection analysis process 500 in FIG. 5 to identify detectability of different foreign objects based on associated atomic numbers, densities, and/or scatter of photons, for example.

The illustration of backscatter x-ray detectability information 800 in FIG. 8 is not meant to imply physical or architectural limitations to the manner in which different advantageous embodiments may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

Figure 9:
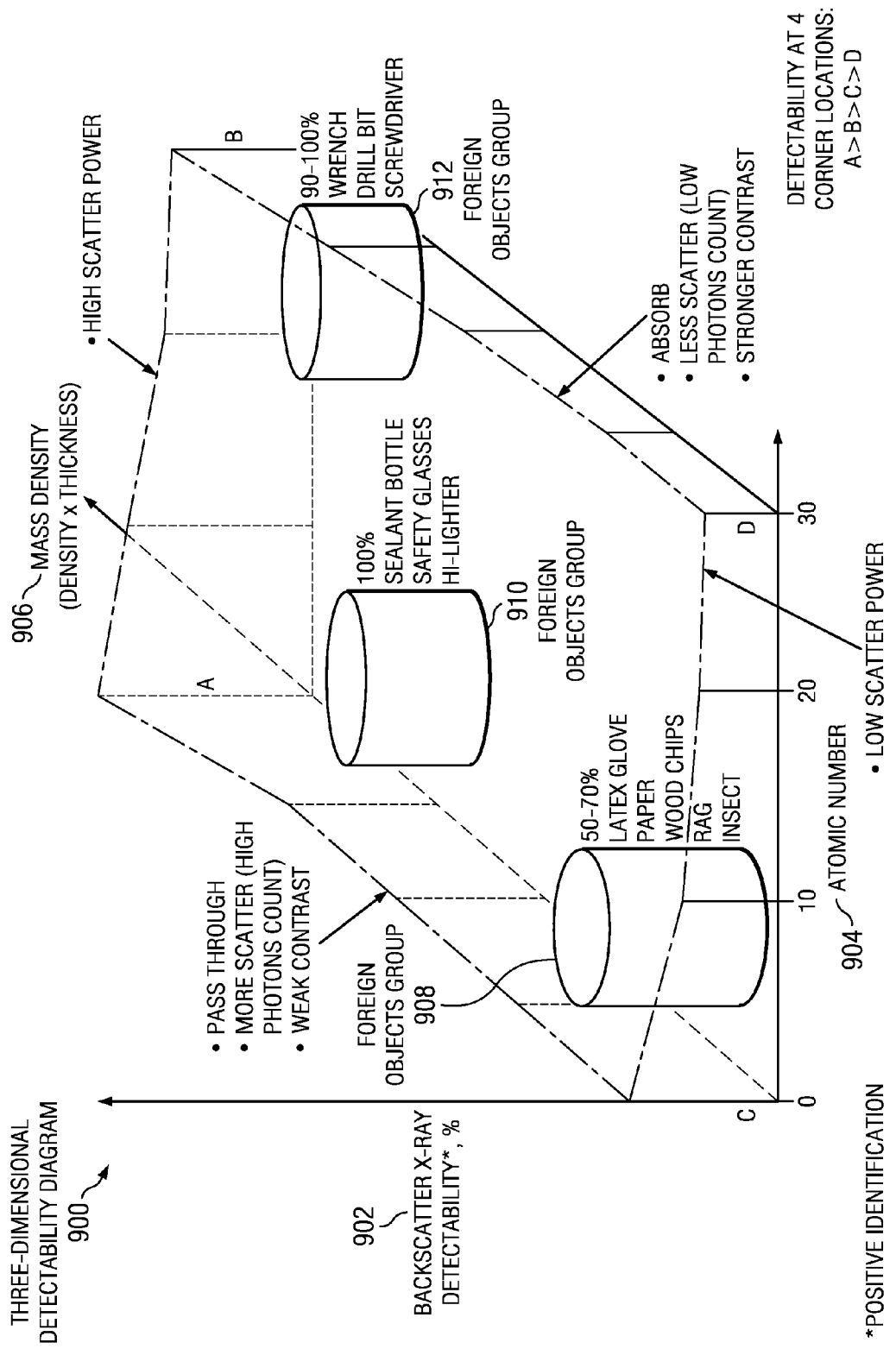
FIG. 9 is an illustration of a three-dimensional detectability diagram in accordance with an advantageous embodiment.

With reference now to FIG. 9, an illustration of a three-dimensional detectability diagram is depicted in accordance with an advantageous embodiment. Three-dimensional detectability diagram 900 is an illustrative example of one implementation of three-dimensional detection probability result 528 generated by three-dimensional diagram generator 514 in FIG. 5.

Three-dimensional detectability diagram 900 is a three-dimensional visual diagram of detectability for a number of objects, such as number of objects 306 in FIG. 3 and/or input object data 504 in FIG. 5, for example. Three-dimensional detectability diagram 900 includes backscatter x-ray detectability 902, atomic number 904, and mass density 906. Three-dimensional detectability diagram 900 presents detectability of foreign objects in a three-dimensional grid, where backscatter x-ray detectability 902 is expressed in percentage along the Z-axis, atomic number 904 is represented along the X-axis, and mass density 906 is represented along the Y-axis.

Foreign objects group 908 includes, for example, without limitation, latex glove, paper, wood chips, rag, and insect. Three-dimensional detectability diagram 900 represents the detectability of foreign objects group 908 as 50-70% detectable based on atomic number 904 and mass density 906. Foreign objects group 908 may be less detectable than other foreign objects because of low density, which provides low scatter power, for example. Foreign objects group 908 may also be less detectable than other foreign objects because the lower atomic number associated with foreign objects group 908 provides more pass through of photons, for example.

Foreign objects group 910 includes, for example, without limitation, sealant bottle, safety glasses, and hi-lighter. Three-dimensional detectability diagram 900 represents the detectability of foreign objects group 910 as 100% detectable based on atomic number 904 and mass density 906. Foreign objects group 910 may be more detectable than foreign objects group 908 because of higher density, for example.

Foreign objects group 912 may include, for example, without limitation, wrench, drill bit, and screw driver. Three-dimensional detectability diagram 900 represents the detectability of foreign objects group 912 as 90-100% detectable based on atomic number 904 and mass density 906. Foreign objects group 912 may be more detectable than foreign objects group 908 because of higher density, for example. Foreign objects group 912 may be slightly less detectable than foreign objects group 910 because of higher atomic numbers, which result in more absorption of photons, for example.

The illustration of three-dimensional detectability diagram 900 in FIG. 9 is not meant to imply physical or architectural limitations to the manner in which different advantageous embodiments may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

Figure 10:
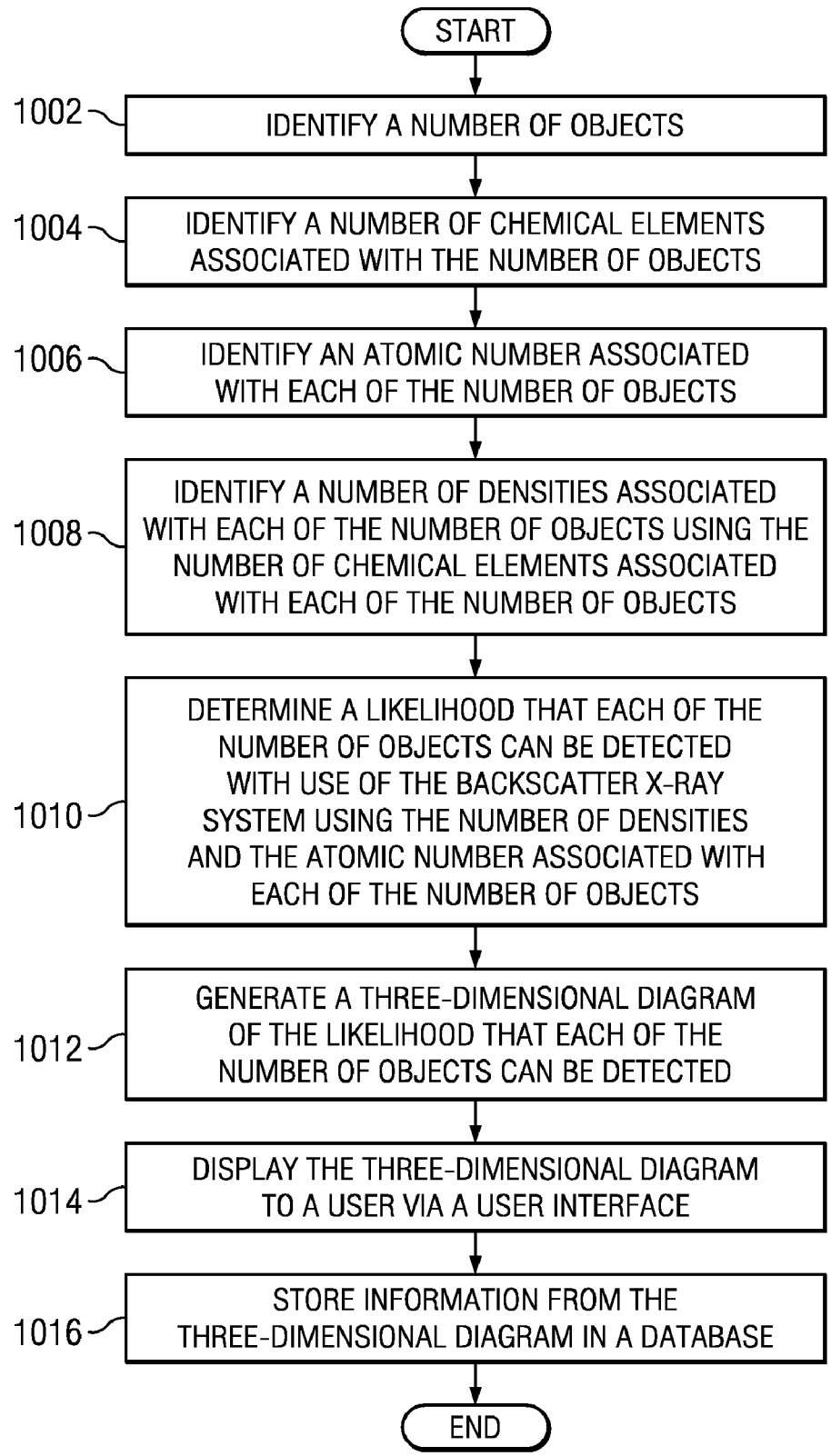
FIG. 10 is an illustration of a flowchart for a process of predicting detection of objects using backscatter x-rays in accordance with an advantageous embodiment.

With reference now to FIG. 10, an illustration of a flowchart for a process of identifying a likelihood that objects can be detected using a backscatter x-ray system is depicted in accordance with an advantageous embodiment. The process in FIG. 10 may be implemented by a component such as detection analysis process 500 in FIG. 5, for example.

The process begins by identifying a number of objects (operation 1002). The number of objects may be, for example, a number of objects not expected or intended to be within a structure, such as number of objects 306 within structure 304 in FIG. 3, for example. The number of objects may be identified through input received from a user, such as input 316 from user 314 in FIG. 3.

The process identifies a number of chemical elements associated with the number of objects (operation 1004). The number of chemical elements may be identified using a database, such as objects related to chemical elements 518 in FIG. 5, for example. The process may use an object identifier, such as object identifier 510 in FIG. 5, to access objects related to chemical elements 518 and identify the number of chemical elements associated with the number of objects identified.

The process identifies an atomic number associated with each of the number of objects (operation 1006). The atomic number may be identified using a database, such as objects related to chemical elements 518 and/or chemical elements and related reference densities 516 in FIG. 5, for example.

The process identifies a number of densities associated with each of the number of objects using the number of chemical elements associated with each of the number of objects (operation 1008). The process may use a density calculator, such as density calculator 508 in FIG. 5, to calculate the density of each object in the number of objects identified. The density calculator may access a database, such as chemical elements and related reference densities 516 in FIG. 5, to identify a number of different densities associated with a number of different chemical elements, in order to calculate the density for each of the number of objects identified.

The process then determines a likelihood that each of the number of objects can be detected with use of the backscatter x-ray system using the number of densities and the atomic number associated with each of the number of objects (operation 1010). The process may use an evaluator, such as photon evaluator 512 in FIG. 5, to access a database, such as backscatter x-ray detectability information 520 in FIG. 5. The evaluator may use detection scales associated with atomic numbers and densities in the database to determine the detectability of each of the number of objects identified, for example.

The process generates a three-dimensional diagram of the likelihood that each of the number of objects can be detected (operation 1012). The three-dimensional diagram may be, for example, three-dimensional detection probability result 528 in FIG. 5 and/or three-dimensional detectability diagram 900 in FIG. 9. The three-dimensional diagram is a visual diagram of the likelihood of detectability by the backscatter x-ray system for each of the number of objects identified.

The process then displays the three-dimensional diagram to a user via a user interface (operation 1014), and stores the information from the three-dimensional diagram in a database (operation 1016) with the process terminating thereafter. The database may be, for example, past three-dimensional detection probability results 530 in FIG. 5.

The illustration of the process in FIG. 10 is not meant to imply physical or architectural limitations to the manner in which different advantageous embodiments may be implemented. Other operations in addition to and/or in place of the ones illustrated may be used. Some operations may be unnecessary in some advantageous embodiments. Also, the operations are presented to illustrate some functional steps. One or more of these operations may be combined and/or divided into different operations when implemented in different advantageous embodiments.

Figure 11:
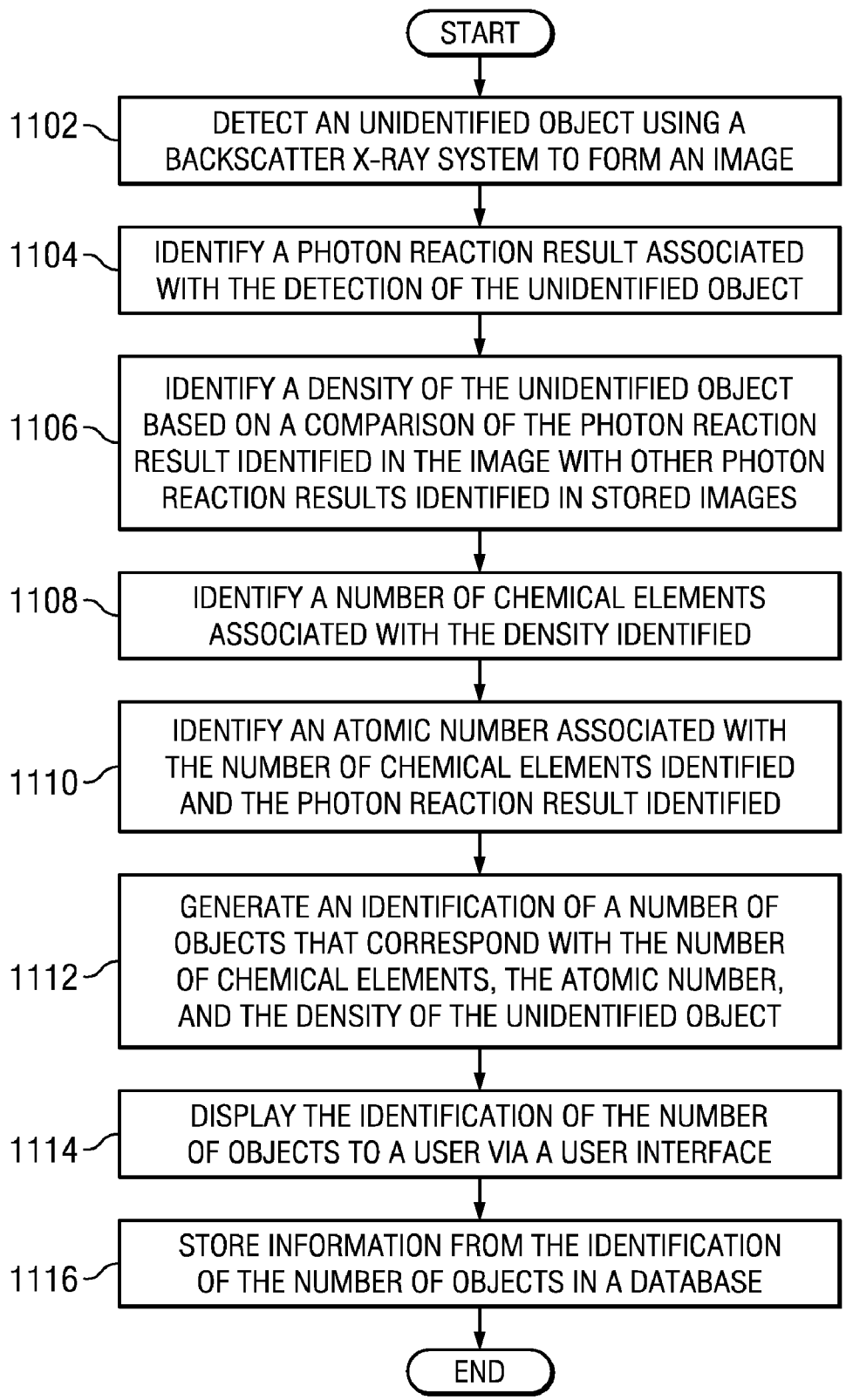
FIG. 11 is an illustration of a flowchart for a process of identifying detected objects in accordance with an advantageous embodiment.

With reference now to FIG. 11, an illustration of a flowchart for a process of identifying objects after the objects are detected is depicted in accordance with an advantageous embodiment. The process in FIG. 11 may be implemented by a component such as detection analysis process 500 in FIG. 5, for example.

The process begins by detecting an unidentified object using a backscatter x-ray system to form an image (operation 1102). The backscatter x-ray system generates an image of a detected object within a structure, such as aircraft 200 in FIG. 2, for example. The image may depict an unidentified object having a certain density and causing a particular photon reaction to backscatter x-rays. The backscatter x-ray system may generate the image from detection through a structural component, such as number of structural components 308 in FIG. 3. In an illustrative example, the backscatter x-ray system may direct photons through a metal plate in order to detect potential unintended objects behind the plate that are not visible or accessible. The detection of these unintended objects is done without requiring disassembly or destruction of parts enclosing the area, or blocking an area from visible view.

The process identifies a photon reaction result associated with the detection of the unidentified object using the image (operation 1104). The photon reaction result may be, for example, a photon count. The process then identifies a density of the unidentified object based on a comparison of the photon reaction result identified in the image with other photon reaction results identified in stored images (operation 1106). The process may retrieve stored images for comparison from a database containing prior object images with associated photon reaction results, or photon counts, and density data, for example, such as images 544 in FIG. 5. The image comparison may focus on, for example, without limitation, image resolution and unique characteristics of the image formed by various types of objects, such as metal and plastic, for example.

The process identifies a number of chemical elements associated with the density identified (operation 1108). The process may use a density calculator, such as density calculator 508 in FIG. 5, to access a database, such as chemical elements and related reference densities 516 in FIG. 5, to determine the number of chemical elements associated with the density of the unidentified object.

The process identifies an atomic number associated with the number of chemical elements identified and the photon reaction result identified (operation 1110). The process may use an object identifier, such as object identifier 510 in FIG. 5, to determine the atomic number associated with the number of chemical elements using a database, such as objects related to chemical elements 518 and/or chemical elements and related reference densities 516 in FIG. 5, for example. The process may use an evaluator, such as photon evaluator 512 in FIG. 5 to determine an atomic number based on the photon reaction result identified, for example.

The process then generates an identification of a number of objects that correspond with the number of chemical elements, the atomic number, and the density of the unidentified object (operation 1112). The identification may be, for example, unidentified object identification result 540 in FIG. 5. The identification may list a number of different objects that are probable matches to the unidentified object based on the information received and determined by the process. The process displays the identification of the number of objects to a user via a user interface (operation 1114). The process then stores the information from the identification of the number of objects in a database (operation 1116) with the process terminating thereafter. The database may be, for example, past unidentified objects identification results 542 in FIG. 5. The process may be prompted by a user to perform iterations to confirm the identification of the unidentified object to a certain degree of likelihood, for example.

The illustration of the process in FIG. 11 is not meant to imply physical or architectural limitations to the manner in which different advantageous embodiments may be implemented. Other operations in addition to and/or in place of the ones illustrated may be used. Some operations may be unnecessary in some advantageous embodiments. Also, the operations are presented to illustrate some functional steps. One or more of these operations may be combined and/or divided into different operations when implemented in different advantageous embodiments.

In one illustrative example, the process may search for similar photon counts in the database of stored images within a predefined range. The associated images to the photon counts within the predefined range may be retrieved and compared to the new image generated through detection of the unidentified object, in this example. The retrieved images may be scanned for similar image resolutions related to photon counts, iteratively narrowing down the selection to the closest match or matches. Object information may then be retrieved for the closest match or matches, such as, for example, density, thickness, atomic number, object name, and/or any other suitable object information.

The flowcharts and block diagrams in the different depicted embodiments illustrate the architecture, functionality, and operation of some possible implementations of apparatus, methods and computer program products. In this regard, each block in the flowchart or block diagrams may represent a module, segment, or portion of computer usable or readable program code, which comprises one or more executable instructions for implementing the specified function or functions. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved.

The different advantageous embodiments provide a method and system for constructing a three-dimensional visual detectability diagram to predict the detectability of potential foreign objects using the atomic numbers and mass densities of the objects.

The different advantageous embodiments can take the form of an entirely hardware embodiment, an entirely software embodiment, or an embodiment containing both hardware and software elements. Some embodiments are implemented in software, which includes but is not limited to forms, such as, for example, firmware, resident software, and microcode.

Furthermore, the different embodiments can take the form of a computer program product accessible from a computer-usable or computer-readable medium providing program code for use by or in connection with a computer or any device or system that executes instructions. For the purposes of this disclosure, a computer-usable or computer readable medium can generally be any tangible apparatus that can contain, store, communicate, propagate, or transport the program for use by or in connection with the instruction execution system, apparatus, or device.

The computer usable or computer readable medium can be, for example, without limitation an electronic, magnetic, optical, electromagnetic, infrared, or semiconductor system, or a propagation medium. Non limiting examples of a computer-readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W) and DVD.

Further, a computer-usable or computer-readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example without limitation, physical or wireless.

A data processing system suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories which provide temporary storage of at least some computer readable or computer usable program code to reduce the number of times code may be retrieved from bulk storage during execution of the code.

Input/output or I/O devices can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems or remote printers or storage devices through intervening private or public networks. Non-limiting examples of modems and network adapters are just a few of the currently available types of communications adapters.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for identifying a likelihood of detecting objects, the method comprising:
    identifying a number of objects using a processor unit;
    identifying a number of densities associated with each of the number of objects using a number of chemical elements associated with the each of the number of objects;
    determining the likelihood of detecting each of the number of objects with a backscatter x-ray system, in which the likelihood is determined using the number of densities and an atomic number associated with the each of the number of objects; and
    generating a three-dimensional diagram of the likelihood of detecting each of the number of objects with the backscatter x-ray system.

2. The method of claim 1, wherein the number of objects are located within a structure.

3. The method of claim 2, wherein the structure is an aircraft.

4. The method of claim 1, further comprising:
identifying the number of chemical elements associated with each of the number of objects using a plurality of databases.

5. The method of claim 1, further comprising:
identifying the atomic number associated with each of the number of objects using a plurality of databases.

6. The method of claim 1, further comprising:
displaying the three-dimensional diagram to a user via a user interface.

7. The method of claim 1, further comprising:
storing information from the three-dimensional diagram in a database.

8. A method for identifying objects after the objects have been detected, the method comprising:
detecting an unidentified object using a backscatter x-ray system to form an image;
identifying a photon reaction result associated with the detection of the unidentified object using the image;
identifying a density of the unidentified object based on a comparison of the photon reaction result identified in the image with other photon reaction results identified in stored images; and
generating an identification of a number of foreign objects associated with the density and the photon reaction result identified.

9. The method of claim 8, wherein the unidentified object is detected within a structure.

10. The method of claim 8, wherein the structure is an aircraft.

11. The method of claim 8, further comprising:
identifying a number of chemical elements associated with the density identified for the unidentified object.

12. The method of claim 11, further comprising:
identifying an atomic number associated with the number of chemical elements identified.

13. The method of claim 8, further comprising:
displaying the identification of the number of foreign objects to a user via a user interface.

14. The method of claim 8, further comprising:
storing information from the identification of the number of foreign objects in a database.

15. A system for identifying a likelihood of detecting objects with a backscatter x-ray system, the system comprising:
a structure having a number of objects;
a plurality of databases; and
a processor unit configured to execute a detection analysis process to identify the number of objects; identify a number of densities associated with each of the number of objects using a number of chemical elements associated with the each of the number of objects; determine the likelihood of detecting each of the number of objects with the backscatter x-ray system using the number of densities and an atomic number associated with the each of the number of objects; and generate a three-dimensional diagram of the likelihood of detecting the number of objects with the backscatter x-ray system.

16. The system of claim 15, wherein the structure is an aircraft.

17. The system of claim 15, wherein the processor unit is further configured to execute the detection analysis process to identify the number of chemical elements associated with each of the number of objects using the plurality of databases.

18. The system of claim 15, wherein the processor unit is further configured to execute the detection analysis process to identify the atomic number associated with each of the number of objects using the plurality of databases.

19. The system of claim 15, wherein the processor unit is further configured to execute the detection analysis process to display the three-dimensional diagram to a user via a user interface.

20. The system of claim 15, wherein the processor unit is further configured to store information from the three-dimensional diagram in a database.

21. A system for identifying objects after the objects have been detected, the system comprising:
a structure having an unidentified object;
a detector configured to detect the unidentified object and generate an image of the unidentified object;
a plurality of databases; and
a processor unit configured to execute a detection analysis process to identify a photon reaction result associated with the detection of the unidentified object using the image; identify a density of the unidentified object based on a comparison of the photon reaction result identified in the image with other photon reaction results identified in stored images; identify a number of chemical elements associated with the density identified for the unidentified object; identify an atomic number associated with the number of chemical elements identified and the photon reaction result identified; and generate an identification of a number of foreign objects that correspond with the number of chemical elements, the atomic number, and the density of the unidentified object.

22. The system of claim 21, wherein the detector is a backscatter x-ray system.

23. The system of claim 21, wherein the structure is an aircraft.

24. The system of claim 21, wherein the processor unit is further configured to execute the detection analysis process to display the prediction of the number of foreign objects to a user via a user interface.

25. The system of claim 21, wherein the number of chemical elements and the atomic number are identified using the plurality of databases.

* * * * *